United States Patent [19]

Ezer et al.

[11] 4,198,402

[45] Apr. 15, 1980

[54] ANTIPHLOGISTIC COMPOSITION OF PHENYLBUTOZONE AND ALKALI SALICYLATE AND METHOD OF TREATMENT

[75] Inventors: Elemer Ezer; Laszio Szporny; Lilla Forgach; Éva Palosi; Eszter Cholnoky; Egon Karpati; György Hajos; Gyozo Hortobagyi; Katalin Gidai, all of Budapest, Hungary

[73] Assignee: Richter Gedeon Vegyeszeti Gyar Rt., Budapest, Hungary

[21] Appl. No.: 892,918

[22] Filed: Apr. 3, 1978

Related U.S. Application Data

[62] Division of Ser. No. 641,771, Dec. 17, 1975, abandoned.

[51] Int. Cl.$^2$ .............................................. A61K 31/62
[52] U.S. Cl. ................................ 424/232; 424/273 P

[58] Field of Search ........................ 424/230, 231, 232

[56] References Cited

PUBLICATIONS

Gietka et al.–Chem. Abst., vol. 82, (1975), p. 291p.
Trinus et al.–Chem. Abst., vol. 77, (1972), p. 135,081n.
Kirichek–Chem. Abst. vol., 76, (1972), p. 121,798u.
Mhirden et al.–Chem. Abst., vol. 82, (1975), p. 38,749g.
Zathurecky et al.–Chem. Abst., vol. 82, (1975), p. 164,817r.

*Primary Examiner*—Sam Rosen
*Attorney, Agent, or Firm*—Karl F. Ross

[57] ABSTRACT

Ulcer production in animals is prevented during prolonged antiphlogistic treatment with ulcerogenic quantities of phenylbutazone by using it in a composition of 1 part of antiphlogistic to 0.2 to 50 parts by weight of alkali metal salicylate.

4 Claims, No Drawings

ANTIPHLOGISTIC COMPOSITION OF PHENYLBUTOZONE AND ALKALI SALICYLATE AND METHOD OF TREATMENT

This is a division of application Ser. No. 641,771, filed Dec. 17, 1975, now abandoned.

This invention relates to new pharmaceutical compositions and to a process for the preparation thereof. More particularly, the invention relates to new pharmaceutical compositions possessing antiphlogistic effects.

As known, all of the hitherto applied antiphlogistic agents have the common disadvantage of causing gastrointestinal haemorrhages or ulcers. The ulcerogenic side-effects of 1-(p-chlorobenzoyl)-5-methoxy-2-methyl-indole-3-yl-acetic acid (indomethacin), 4-butyl-1,2-diphenyl-pyrazolidine-3,5-dione (phenylbutazone) and acetylsalicylic acid have been reported in numerous publications (Bonfils et al.: Bull. Mem. Soc. Med. Hosp. Paris, 5, 114 (1955); Somogyi et al.: J. Pharm. Pharmacol. 21, 122 (1969); R. Nath: Studies on the Pharmacology of Inflammation, M.D. Thesis Lucknow University, Lucknow, India (1970); Lee et al.: Arch. Int. Pharmacodyn. 19, 370 (1971); Bhargava et al.: European J. of Pharmacol. 22, 191 (1973); Katz et al.: Clin. Pharm. Ther. 6, 25 (1965); Leonard et al.: Clin. Pharmacol. Ther. 14, No. 1, 62 (1973).

In prolonged treatments of various arthritic conditions two or more different antiphlogistic agents can sometimes be administered simultaneously to the patients. The antiphlogistic effects arising upon the simultaneous administration of indomethacin and acetylsalicylic acid were investigated first in animal tests (Mielons et al.: J. Pharm. Pharmac. 20, 567 (1968); Swingle et al.: J. Pharmacol. Exp. Ther. 172, 423 (1970); Yesair et al.: Biochem. Pharm. 19, 1591 (1970). Since the oedema tests had not indicated the additivity of antiphlogistic effects, clinical tests were performed in order to elucidate this question (Champion et al.: Clin. Pharm. and Ther. 13, 239 (1972); Lindquist et al.; Clin. Pharm. and Ther. 15, 247 (1974). These clinical tests have shown that the blood indomethacine level is not affected by the simultaneous administration of acetylsalicylic acid, that is, these two types of antiphlogistic agents do not worsen the effects of one another.

So far only the main effect, i.e. the antiphlogistic activity was investigated in the tests utilizing two different antiphlogistic agents simultaneously, and the gastrointestinal side-effects have not been analyzed. Our experiments aimed at investigating both the main antiphlogistic effect and the ulcerogenic side-effects appearing upon the administration of various combinations of antiphlogistic agents, and preparing a pharmaceutical composition in which the original antiphlogistic effects of the individual components are retained but the gastrointestinal side-effects are decreased to the minimum. The primary subjects of these experiments were the most widely applied antiphlogistic agents, i.e. the salicylates (particularly acetylsalicylic acid) and indomethacin.

The antiphlogistic effects were studied on Wister rats of both sexes, each weighing 100 to 150 g. The animals were starved for 24 hours, and then 0.1 ml portions of a 1% carrageenin solution were injected under mild ether anaesthesia into the plantar region of one of the hind paws in order to provoke inflammation (oedema). The antiphlogistic agent or a combination thereof was introduced into the stomach of the animals via a stomach tube immediately before injecting the carrageenine solution. 4 hours after this treatment the animals were sacrified, and both hind paws were amputated above the ankles. The paws were weighed, and the oedema weight was calculated from the weight difference of the treated and untreated paws.

The gastrointestinal ulcerogenic side-effects of the individual active agents and their combinations were also examined on Wistar rats weighing 100 to 150 g. The animals were starved for 24 hours, and the substances to be tested were administered to them via a stomach tube. 4 hours after the treatment the animals were sacrified, the stomach was removed, incised along the greater curvature, washed, and the haemorrhages (brown spots) appearing on the glandular part were counted. The results were subjected to Student's "t"-test.

The ulcerogenic side-effects of the individual antiphlogistic agents were examined first by these tests. The results are summarized in Table 1. As it appears from the data of the Table, all the compounds examined possess more or less pronounced ulcerogenic side-effects.

Table 1

| Ulcerogenic side-effects of various antiphlogistic agents | | | | | |
|---|---|---|---|---|---|
| Compound | No. of test animals | Dosage mg/kg p.o. | No. of ulcer/ stomach | Ulcer-free No. | animals % |
| Indomethacin | 20 | 5 | 1.1 | 15 | 72 |
| " | 28 | 10 | 6.5 | 5 | 18 |
| " | 120 | 20 | 15.0 | 6 | 5 |
| " | 41 | 30 | 24 | 0 | 0 |
| Nifluminic acid | 18 | 12.5 | 0.6 | 14 | 78 |
| " | 16 | 25 | 10.2 | 2 | 12 |
| " | 15 | 50 | 19.0 | 0 | 0 |
| " | 15 | 100 | 23.0 | 0 | 0 |
| Phenylbutazone | 18 | 25 | 0.5 | 13 | 73 |
| " | 16 | 50 | 0.6 | 4 | 25 |
| " | 17 | 100 | 6.5 | 4 | 23 |
| " | 15 | 200 | 20.0 | 1 | 7 |
| Aspirin | 25 | 25 | 4.7 | 2 | 8 |
| " | 25 | 50 | 5.4 | 3 | 10 |
| " | 120 | 100 | 6.5 | 18 | 14 |
| " | 58 | 400 | 11.0 | 7 | 12 |
| Sodium salicylate | 45 | 50 | 0.1 | 37 | 82 |
| " | 28 | 100 | 0.1 | 27 | 96 |
| " | 64 | 200 | 1.2 | 37 | 50 |
| " | 45 | 400 | 1.1 | 32 | 71 |

The following tests aimed at investigating the effects which appear upon the administration of two different antiphlogistic agents in combination with each other. In the first tests combinations of indomethacin and sodium salicylate were studied. It has been found, unexpectedly, that these compounds mutually suppress the ulcerogenic side-effects of one another, while leaving the main antiphlogistic effects unchanged. This fact could not be foreseen at all, since it is well known that the above two compounds possess marked ulcerogenic side-effects when added separately.

In the tests the animals received the same dosages of indomethacin, and the amount of sodium salicylate administered was varied. It has been found that the number of ulcer-free animals increases proportionally to the increase in the amount of sodium salicylate added, and when sodium salicylate is administered in a 20-fold amount with respect to indomethacin, the ulcerogenic effect disappears completely, i.e. sodium salicylate antagonizes entirely the deleterious side-effect of indomethacin. Table 2 shows the ulcerogenic effects and Table 3 shows the antiphlogistic effects of combinations containing varying amounts of sodium salicylate besides indomethacine.

Table 2

Inhibition of indomethacin-indiced ulcer by the simultaneous administration of sodium salicylate

| No. of animals tested | Dosage, mg/kg p.o. | | Ulcerogeneous side-effect | | Ulcer-free animals | |
|---|---|---|---|---|---|---|
| | Indo-methacin | Sodium salicylate | No. of ulcer/stomach | Inhibition | No. | % |
| 120 | 20 | — | 15.0 ± 0.5$^{xx}$ | — | 6 | 5 |
| 17 | 20 | 25 | 6.1 ± 1.3$^{xx}$ | 60$^x$ | 2 | 12 |
| 18 | 20 | 50 | 7.5 ± 1.4$^{xx}$ | 50$^x$ | 2 | 10 |
| 22 | 20 | 100 | 4.0 ± 0.8$^{xx}$ | 73$^x$ | 3 | 13 |
| 58 | 20 | 200 | 0.27 ± 0.1$^{xx}$ | 98$^x$ | 51 | 88 |
| 22 | 20 | 400 | 0 | 100$^x$ | 22 | 100 |

$^x p < 0.01$ (significance level determined by Student's "t"-test)
$^{xx}$ corrected with the mean standard error Table 3

Antiphlogistic effects of sodium salicylate, indomethacin and combinations thereof determined by carrageenin-oedeme test

| Dosage of the compounds tested mg/kg p.o. | | No. of animals tested | Oedema-inhibiting effect % |
|---|---|---|---|
| Sodium salicylate | Indomethacin | | |
| 50 | — | 31 | 15 |
| 100 | — | 28 | 43$^x$ |
| — | 5 | 21 | 40$^x$ |
| — | 10 | 28 | 45$^x$ |
| 50 | 5 | 29 | 40$^x$ |
| 200 | 5 | 10 | 41$^x$ |

$^x p < 0.05$ (significance level determined by Student's "t"-test)

In the following tests animals treated for 3 days with various combinations of indomethacin and sodium salicylate were examined. The non-starved test animals were treated orally for 3 days with compositions containing 20 mg/kg of indomethacin and increasing amounts of sodium salicylate. 73% of the animals receiving only indomethacin died on the 3rd day in peritonitis resulting from intestinal perforation, and clearly visible ulcers appeared in the intestines of the survivals. In contrast, when indomethacin was administered in combination with sodium salicylate, this severe side-effect could be antagonized completely. The results are summarized in Table 4.

Table 4

Antagonizing the gastrointestinal side-effects of indomethacin by sodium salicylate administered simultaneously (tests performed for 3 days on non-starved animals)

| No. of animals tested | Dosage mg/kg p.o. | | Died | | Ulcerous animals | |
|---|---|---|---|---|---|---|
| | Indo-methacin | Sodium salicylate | No. | % | No. | % |
| 45 | 3 × 20 | — | 33 | 73 | 45 | 100 |
| 20 | 3 × 20 | 3 × 50 | 5 | 25 | 11 | 55 |
| 20 | 3 × 20 | 3 × 100 | 3 | 15 | 3 | 15 |
| 45 | 3 × 20 | 3 × 200 | 0 | 0 | 0 | 0 |

It has also been studied whether sodium salicylate also antagonizes the ulcerogenic side-effects of antiphlogistic agents other than indomethacin. These tests have shown that the ulcerogenic side-effects of phenylbutazone, nifulmic acid and acetylsalicylic acid (aspirin) or its salts can also be antagonized effectively by administering them together with sodium salicylate, and the main antiphlogistic effects of these compounds remain unchanged, or even the antiphlogistic effects of the two active agents are superimposed. It is particularly surprising that the salts of salicylic acid exert a protective effect even against ulcers provoked by acetylsalicylic acid, i.e. two different salicylic acid derivatives mutually suppress the harmful side-effects of each other. The results of these tests are summarized in Tables 5 to 7.

Table 5

Antagonizing the ulcerogenic side-effects of phenylbutazone and nifumic acid by sodium salicylate administered simultaneously

| No. of animals tested | Dosage, mg/kg p.o. | | Ulcerogenic side-effect | | Ulcer-free animals | |
|---|---|---|---|---|---|---|
| | Phenyl-butazone | Sodium salicylate | No. of ulcer/stomach | Inhibition % | No. | % |
| 17 | 100 | — | 6.5 | — | 4 | 23 |
| 30 | 100 | 50 | 4.4 | 32 | 8 | 27 |
| 20 | 100 | 100 | 3.3 | 50 | 8 | 40 |
| 18 | 100 | 200 | 2.8 | 57 | 10 | 56 |
| | Nifluminic acid | | | | | |
| 25 | 50 | — | 19 | — | 0 | 0 |
| 20 | 50 | 50 | 21 | — | 0 | 0 |
| 20 | 50 | 100 | 13 | 40 | 0 | 0 |
| 20 | 50 | 200 | 5.5 | 73 | 6 | 30 |

Table 6

Antagonizing the ulcerogenic side-effects of acetylsalicylic acid by sodium salicylate administered simultaneously

| No. of animals tested | Dosage, mg/kg p.o. | | Ulcerogenic side-effect | | Ulcer-free animals | |
|---|---|---|---|---|---|---|
| | Acetylsalicylic acid | Sodium salicylate | No. of ulcer/stomach | Inhibition % | No. | % |
| 120 | 100 | — | 6.5 ± 0.7 | — | 18 | 14 |
| 22 | 100 | 25 | 2.5 × 0.5$^x$ | 58 | 3 | 15 |
| 36 | 100 | 50 | 2.4 ± 0.6$^x$ | 60 | 16 | 45 |
| 31 | 100 | 100 | 0.2 ± 0.1$^x$ | 99 | 29 | 97 |
| 40 | 100 | 200 | 0.3 ± 0.1$^x$ | 98 | 36 | 90 |

$^x p < 0.01$ (significance level determined by Student's "t"-test)

Table 7

Antiphlogistic effects of sodium salicylate, acetylsalicylic acid and combinations thereof determined by carrageenin-oedema test

| Dosage mg/kg p.o. | | No. of animals tested | Inhibition of oedema % |
|---|---|---|---|
| Sodium salicylate | Acetylsalicylic acid | | |
| 50 | — | 31 | 15 |
| 100 | — | 28 | 43$^x$ |
| — | 50 | 13 | 15 |
| — | 100 | 23 | 20$^x$ |
| 50 | 50 | 50 | 21$^x$ |
| 100 | 100 | 100 | 39$^x$ |

$^x p < 0.05$ (significance level determined by Student's "t" test)

The results listed above prove unambiguously that sodium salicylate antagonizes the gastrointestinal haemorrhagic or ulcerogenic side-effects of other non-steroidal antiphlogistic agents, without affecting the main antiphlogistic effect. Similar effects are shown by compositions which contain other salicylic acid salts, or in certain cases even salicylic acid itself, instead of sodium salicylate.

Thus the invention relates to pharmaceutical compositions containing as active agent a non-steroidal antiphlogistic substance or a pharmaceutically acceptable salt thereof and salicylic acid or an alkali salicylate in an amount of 0.2 to 50 parts by weight calculated for one part by weight of said non-steroidal antiphlogistic substance, optionally together with another biologically active substance or a carrier or diluents.

As alkali salicylate preferably sodium or lithium salicylate is applied.

The above compositions can be prepared by methods commonly applied in the pharmaceutical industry. The pharmaceutical compositions can be presented e.g. in the form of tablets, sugar- or film-coated tablets, capsules, suppositories, injectable solutions, etc.

The pharmaceutical compositions according to the invention can be administered orally, rectally and/or parenterally either in a single dosage or in subdivided forms. For oral administration the compositions are presented preferably in the form of tablets, sugar- or film-coated tablets, or capsules. Film-coated tablets are particularly preferable unit dosage forms. These orally administerable compositions contain generally no filler, but in some cases conventional filling agents, e.g. lactose or starch can also be admixed to them. As binding or granulating agent e.g. gelatine, sodium carboxymethylcellulose, methyl cellulose, polyvinylpyrrolidone or gellified starch can be used. The most appropriate disintegrating agents are potato starch and microcrystalline cellulose, but other disintegrating agents, such as ultraamylopectine, formaldehyde-caseine condensates, etc. can be used as well. As lubricating and antiadhesive substances e.g. talc, colloidal silicic acid, stearine, calcium or magnesium stearate, etc. can be used.

The tablets can be prepared e.g. by the conventional wet granulation-compression method. In this instance a dry blend of the active agents, fillers and optionally a part of the disintegrating agents is kneaded with an aqueous, alcoholic or aqueous-alcoholic solution of the appropriate binding agent, the mass is granulated, and the obtained granules are dried. Thereafter the other additives (e.g. the remaining part of the disintegrating agents, lubricants, antiadhesive substances, etc.) are blended with the granular substance, and the blend is compressed into tablets. If desired, the tablets can be provided with parting incisions in order to facilitate their division at administration. If desired, the tablets can be film-coated with substances resistant towards gastric juice, such as shellac, cellulose-acetate phthalate or Eudragit-L$^R$. These film-forming substances are usually deposited onto the tablet from an alcohol, particularly isopropanol solution.

From the appropriate combinations of the active agents and additives the tablets can also be prepared by direct pressing method, and, if desired, the resulting tablets can be provided with an intestinosolvent coating.

If desired, the tablets can be coated with conventional protecting, flavouring and/or colouring agents, such as sugar, cellulose derivatives (methyl or ethylcellulose, sodium carboxymethylcellulose, etc.), polyvinylpyrrolidone, calcium phosphate, calcium carbonate, coloring agents and varnishes commonly used in the food and pharmaceutical industry, iron oxide pigments, aroma substances, etc. For the sake of convenience the thus-obtained coated tablets are referred to in the specification and claims as "sugar-coated tablets", with the understanding that this term also covers coated tablets which contain no sugar in the coating layer.

Capsules are prepared by filling the mixture of the active agents into hard gelatine capsules.

Compositions for rectal administration are presented in the form of suppositories. The suppositories contain, besides the active agents, conventional carriers, such as vegetable fats (e.g. hardened vegetable oils) or triglycerides of $C_{12-18}$ fatty acids. Witepsol$^R$ proved to be a particularly preferable carrier for the preparation of suppositories. The active agents are homogenized with the molten carrier, and the mass is cast into suppository molds.

Compositions for parenteral administration are presented in injectable forms. To prepare injectable solutions the active agents are dissolved e.g. in distilled water and/or various organic solvents, such as lower aliphatic alcohols or glycol ethers (particularly ethyleneglycol monoethyl ether), optionally containing dissolution aids, such as polyoxyethylene sorbitan monolaurate, monooleate or monostearate (Tween 20$^R$, Tween 60$^R$ or Tween 80$^R$). The injectable solutions may contain various other additives, such as preserving agents (e.g. benzyl alcohol, methyl or propyl p-hydroxybenzoate, phenylmercuric borate or benzalkonium chloride), antioxidants (e.g. sodium pyrosulfate, ascorbic acid, tocoferol, etc.), complexing agents for binding traces of heavy metals (e.g. ethylenediamine tetraacetate), substances for adjusting the pH, buffers, and optionally local anaesthetic agents (e.g. lidocaine).

The injectable solutions are filtered, filled into vials, the vials are closed and sterilized.

The invention is elucidated in detail by the aid of the following non-limiting Examples:

EXAMPLE 1

Film-coated tablets containing indomethacin and sodium salicylate as active agents Composition of one tablet:

| | |
|---|---|
| indomethacine | 20 mg |
| sodium salicylate | 200 mg |
| magnesium stearate | 3 mg |
| polyvinyl pyrrolidone | 8 mg |
| Eudragit-L$^R$ | 10 mg |
| talc | 12 mg |
| potato starch | 157 mg |
| total | 410 mg |

The tablets are prepared by the conventional wet granulation-compression technique, and film-coated with Eudragit-L$^R$.

In the above composition sodium salicylate can be repaced by another alkali salicylate, such as lithium salicylate to obtain tablets with the same effect.

EXAMPLE 2

Suppositories containing indomethacin and sodium salicylate as active agents

Composition of one suppository:

| | |
|---|---|
| indomethacine | 0.02 g |
| sodium salicylate | 0.20 g |
| Witepsol H-15$^R$ | 1.78 g |
| total | 2.00 g |

The above components are admixed with each other and the mixture is cast into suppository molds.

In the above composition sodium salicylate can be replaced by lithium salicylate.

EXAMPLE 3

Film-coated tablets containing acetylsalicylic acid and sodium salicylate as active agents Composition of one tablet:

| | | |
|---|---|---|
| acetylsalicylic acid | 200 mg | |
| sodium salicylate | 200 mg | |
| magnesium stearate | 4 mg | |
| Eudragit-L$^R$ | 15 mg | |
| talc | 18 mg | |
| polyvinylpyrrolidone | 20 mg | |
| potato starch | 58 mg | |
| microcrystalline cellulose | 100 mg | |
| total | 615 mg | |

The tablets are prepared by direct pressing and film-coated with Eudragit-L$^R$ to obtain intestinosolvent compositions.

Tablets containing another alkali salicylate instead of sodium salicylate, or containing a salt (e.g. calcium salt) of acetylsalicylic acid instead of the free acid can be prepared by similar methods.

EXAMPLE 4

Suppositories containing acetylsalicylic acid and sodium salicylate as active agents Composition of one suppository:

| | | |
|---|---|---|
| acetylsalicylic acid | 0.2 g | |
| sodium salicylate | 0.2 g | |
| Witepsol H-15$^R$ | 1.6 g | |
| total | 2.0 g | |

The suppositories are prepared as described in Example 2. Suppositories containing calcium acetylsalicylate instead of the free acid, or another alkali salicylate instead of sodium salicylate can be prepared by completely analogous methods.

EXAMPLE 5

Film-coated tablets containing acetylsalicylic acid and sodium salicylate as active agents Composition of one tablet:

| | | |
|---|---|---|
| acetylsalicylic acid | 200 mg | |
| sodium salicylate | 300 mg | |
| magnesium stearate | 5 mg | |
| talc | 20 mg | |
| Eudragit-L$^R$ | 20 mg | |
| polyvinyl pyrrolidone | 25 mg | |
| potato starch | 100 mg | |
| microcrystalline cellulose | 150 mg | |
| total | 820 mg | |

The intestinosolvent tablets are prepared as described in Example 3.

EXAMPLE 6

Film-coated tablets containing phenylbutazone and sodium salicylate as active agents Composition of one tablet:

| | | |
|---|---|---|
| phenylbutazone | 100 mg | |
| sodium salicylate | 250 mg | |
| magnesium stearate | 3 mg | |
| polyvinyl pyrrolidone | 10 mg | |
| talc | 15 mg | |
| Eudragit-L$^R$ | 15 mg | |
| potato starch | 122 mg | |
| total | 515 mg | |

The intestinosolvent tablets are prepared as described in Example 1.

In the above composition phenylbutazone may be replaced by its sodium or calcium salt, and sodium salicylate may be replaced by salicylic acid or lithium salicylate.

EXAMPLE 7

Injectable compositions containing phenylbutazone and sodium salicylate as active agents Composition of one unit dosage:

| | | |
|---|---|---|
| phenylbutazone | 100 mg | |
| sodium salicylate | 250 mg | |
| sodium pyrosulfite | 0.3 mg | |
| ethylenediamine tetraacetate | 0.6 mg | |
| lidocaine hydrochloride | 6.0 mg | |
| sodium hydroxide | 14.0 mg | |
| benzyl alcohol | 30.0 mg | |
| ethyleneglycol monoethylether | 1000.0 mg | |
| distilled water, pro inj. | 3.0 ml | |

Phenylbutazone is dissolved in sodium hydroxide solution under heating, and ethyleneglycol monoethylether is added to the solution. In paralle, sodium salicylate, sodium pyrosulfite and ethylenediamine tetraacetate are dissolved in a part of the distilled water (oxygen-free and saturated with nitrogen). The two solutions are combined, then a solution of lidocaine hydrochloride in the remainder of the distilled water, and finally the benzyl alcohol are added. The solution is filtered, filled into dark vials, the vials are closed and sterilized by heating.

In the above composition sodium salicylate can be replaced by another alkali salicylate. Similarly, phenylbutazone can be replaced by a salt thereof.

EXAMPLE 8

Film-coated tablets containing nifluminic acid and sodium salicylate as active agents Composition of one tablet:

| | | |
|---|---|---|
| nifluminic acid | 150 mg | |
| sodium salicylate | 250 mg | |
| magnesium stearate | 3 mg | |
| polyvinyl pyrrolidone | 12 mg | |
| Eudragit-L® | 15 mg | |
| talc | 18 mg | |
| potato starch | 167 mg | |
| total | 615 mg | |

The intestinosolvent tablets are prepared as described in Example 1.

What we claim is:

1. A pharmaceutical composition containing as the active ingredient a combination of one part by weight of phenylbutazone or a pharmaceutically acceptable salt thereof and 0.2 to 50 parts by weight of an alkali salicylate in effective amounts to reduce ulcer-lesion formation and at the same time being antiflammatory.

2. The composition defined in claim 1 wherein said ingredient is a combination of phenylbutazone and sodium salicylate in effective amounts to reduce ulcer-lesion formation and at the same time being antiflammatory.

3. A method of treating an animal subject for an inflammatory condition without ulcerogenesis and for reducing the tendency to ulcer-lesion formation in antiflammatory treatments with ulcerogenic compounds which comprises administering to said subject an effective amount of a combination of one part by weight of phenylbutazone or a pharmaceutically acceptable salt thereof and 0.2 to 50 parts by weight of an alkali-metal salicylate.

4. The method defined in claim 3 wherein the combination phenylbutazone and sodium salicylate is administered to said subject.

* * * * *